(12) United States Patent
Nakagawa et al.

(10) Patent No.: US 7,064,141 B1
(45) Date of Patent: Jun. 20, 2006

(54) METHOD FOR PREVENTING, TREATING OR INHIBITING DEVELOPMENT OF SIMPLE RETINOPATHY AND PREPROLIFERATIVE RETINOPATHY

(75) Inventors: Shizue Nakagawa, Osaka (JP); Yasutaka Nagisa, Higashiosaka (JP); Hitoshi Ikeda, Higashiosaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 09/958,740

(22) PCT Filed: Apr. 27, 2000

(86) PCT No.: PCT/JP00/02766

§ 371 (c)(1),
(2), (4) Date: Oct. 16, 2001

(87) PCT Pub. No.: WO00/66161

PCT Pub. Date: Nov. 9, 2000

(30) Foreign Application Priority Data

Apr. 28, 1999 (JP) ................................. 11/121498

(51) Int. Cl.
*A61K 31/41* (2006.01)

(52) U.S. Cl. ...................... 514/381; 514/396; 514/397; 514/912

(58) Field of Classification Search ................ 514/381, 514/382, 396, 397, 912
See application file for complete search history.

(56) References Cited

U.S. PATENT DOCUMENTS

| 5,591,762 A | 1/1997 | Hauel et al. |
| 5,889,020 A | 3/1999 | Huxley et al. .............. 514/303 |

FOREIGN PATENT DOCUMENTS

| EP | 0 855 392 | 7/1988 |
| EP | 0 514 216 | 11/1992 |
| EP | 0 631 780 | 1/1994 |
| HU | 217816 | 9/1993 |
| JP | 7-89957 | 4/1995 |
| JP | 2000-159671 | 6/2000 |
| RU | 2124007 | 12/1998 |
| WO | 92/10183 | 6/1992 |
| WO | 93/15732 | 8/1993 |
| WO | 94/11369 | 5/1994 |
| WO | 97/37688 | 10/1997 |
| WO | 98/13356 | 4/1998 |
| WO | 99/00383 | 1/1999 |
| WO | 99/01459 | 1/1999 |
| WO | 99/44590 | 9/1999 |
| WO | 2000/02543 | 1/2000 |
| WO | 2000/16773 | 3/2000 |

OTHER PUBLICATIONS

English translation of The 98th Kanto Area regional Meeting (May 12, 2000), C-5.
The 98th Kanto Area regional Meeting (May 12, 2000), C-5.
R. Klein et al., "Diabetic Eye Disease", The Lancet, vol. 350, No. 9072, Jul. 19, 1997, pp. 197-204.

*Primary Examiner*—Zohreh Fay
(74) *Attorney, Agent, or Firm*—Wenderoth, Lind & Ponack, L.L.P.

(57) ABSTRACT

To provide a pharmaceutical composition for preventing, treating or development-inhibiting simple retinopathy or preproliferative retinopathy, comprising a compound having angiotensin II antagonistic activity, or a salt thereof.

2 Claims, No Drawings

METHOD FOR PREVENTING, TREATING OR INHIBITING DEVELOPMENT OF SIMPLE RETINOPATHY AND PREPROLIFERATIVE RETINOPATHY

This application is a 371 of PCT/JP00/02766 filed Apr. 27, 2000.

TECHNICAL FIELD

The present invention relates to a pharmaceutical composition for preventing, treating or development-inhibiting simple retinopathy and preproliferative retinopathy, which comprises a compound having angiotensin II antagonistic activity, or a salt thereof, as an active ingredient.

BACKGROUND ART

Diabetic retinopathy is a diabetic complication which is caused by microangiopathy due to hyperglycemia, and the number of diabetic patients suffering from complicated diabetic retinopathy is increasing while the duration of diabetes becomes longer and longer. It is reported that not less than 80% of diabetic patients will suffer from retinopathy coincided with diabetes until two decades will have passed since the development of diabetes. Diabetic retinopathy develops to simple retinopathy, preproliferative retinopathy and proliferative retinopathy. In simple retinopathy, increase of vascular permeability, retinal edema, thickening of basement membrane, disorder in vascular endothelial cell, dropout of pericyte, etc. are observed. When deterioration of retinal potential (visual function) followed by vascular obstruction is observed, preproliferative retinopathy is diagnosed, which finally develops to proliferative retinopathy in which connective tissue membrane proliferation and neovascularization are observed. Proliferative retinopathy is, in some cases, accompanied by retinal detachment. The patients feel no subjective symptom to proliferative retinopathy. Therefore, when they have felt abnormality in the eyes, it is too late in many cases. Thus, it is very important to prevent or treat retinopathy or inhibit the development thereof in an early stage. Further, diabetic retinopathy is the primary cause of adult-onset blindness, and it induces a serious social problem in view of comfortable social life.

As the main treatments of diabetic retinopathy at present, photocoagulation using laser is done when neovascularization is observed in funduscopy, or a vitrectomy is done when diabetes has been developed with fibloblast membrane proliferation and retinal detachment observed. However, treatment by photocoagulation or a vitrectomy is in some cases impossible depending on the site affected by the disease, and in other cases, vision has not been restored even if the surgical treatment is succeeded. Under these circumstances, development of a pharmaceutical composition capable of treating diabetic retinopathy in an early stage is desired.

The compounds having angiotensin II antagonistic activities are known as agents for treating circulatory diseases such as hypertension, cardiac diseases (e.g., cardiomegaly, cardiac failure, cardiac infraction, etc.), cerebral hemorrhage, nephritis, etc. (refer to Japanese Unexamined Patent Publication No. 4-364171/1992 etc.). It is believed that the mechanism of action of such a compound would be actuated by inhibiting the binding of angiotensin II having a strong vasoconstriction to an angiotensin II receptor.

Diabetic patients have complicated hypertension at a higher frequency than non-diabetic patients, and hypertension is one of significantly critical factors for causing the onset and development of retinopathy. The diabetic patients with complicated retinopathy have higher blood levels of angiotensin-converting enzymes capable of producing angiotensin II having strong vasoconstriction than non-diabetic patients, and out of the diabetic patients, the patients having proliferative retinopathy tend to have higher blood levels of such enzymes than the patients without proliferative retinopathy.

Recently, researches for elucidating the pathology of diabetic retinopathy have been advanced, and it is believed that a vascular endothelial growth factor (VEGF), which exhibits potential endothelial cell growing action and vascular permeability increasing action, would induce proliferative retinopathy which is an terminal symptom of diabetic retinopathy, because of its physiological actions, an increase in the vitreous VEGF level of the patients with proliferative retinopathy, and increase of expression of VEGF on the retina of animal models. VEGF also has potential vascular permeability increasing action, and VEGF is considered to cause retinal edema observed in simple retinopathy or preproliferative retinopathy. It is reported that an individual renin-angiotensin system is found in the retina, and it becomes an evident that angiotensin II accelerates the production of VEGF in the retinal tissue. These facts suggest that the renin-angiotensin system is involved in diabetic retinopathy.

DISCLOSURE OF INVENTION

The present invention provides a pharmaceutical composition useful for preventing, treating or development-inhibiting simple retinopathy or preproliferative retinopathy.

Under the foregoing circumstances, the present inventors have intensively researched pharmaceutical compositions useful for preventing, treating or development-inhibiting simple retinopathy or preproliferative retinopathy, and as a result, found that the use of a compound having angiotensin II antagonistic activity, particularly a compound having angiotensin II antagonistic activity of a specific formula is very effective to not only improve retinal potential (visual function) and retinal edema (disorder in tissue) but also prevent, treat or development-inhibit simple retinopathy or preproliferative retinopathy. They have further progressively researched based on the above findings, and accomplished the present invention. That is, the present invention relates to the following.

(1) A pharmaceutical composition for preventing, treating or development-inhibiting simple retinopathy or preproliferative retinopathy, which comprises the compound having angiotensin II antagonistic activity (the compound having angiotensin II receptor antagonistic activity) or prodrug thereof, or a salt thereof;

(2) the composition of the above (1), wherein the compound having angiotensin II antagonistic activity is a non-peptide compound;

(3) the composition of the above (1), wherein the compound having angiotensin II antagonistic activity is a compound having an oxygen atom in its molecule;

(4) the composition of the above (1), wherein the compound having angiotensin II antagonistic activity is a compound having an ether linkage or a carbonyl group;

(5) the composition of the above (1), wherein the compound having angiotensin II antagonistic activity is a compound of the formula (I):

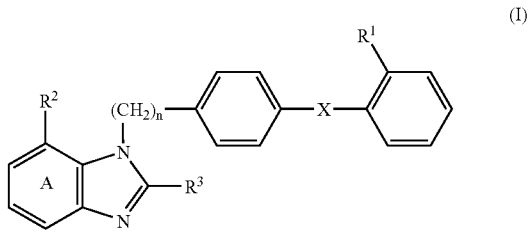

wherein R¹ is a group capable of forming an anion or a group capable of converting thereinto, X shows that the phenylene group and the phenyl group bind to each other directly or through a spacer having an atomic chain length of 2 or less, n is an integer of 1 or 2, the ring A is a benzene ring having an optional substitution, in addition to the group R², R² is a group capable of forming an anion or a group capable of converting thereinto, and R³ is an optionally substituted hydrocarbon residue which may bind through a hetero-atom;

(6) the composition of the above (1), wherein the compound having angiotensin II antagonistic activity is Losartan, Eprosartan, Candesartan, Candesartan cilexetil, Valsartan, Telmisartan, Irbesartan or Tasosartan;

(7) the composition of the above (1), wherein the compound having angiotensin II antagonistic activity is 2-ethoxy-1-[[2'-(1H-tetrazol-5-yl)biphenyl-4-yl]methyl]benzimidazole-7-carboxylic acid;

(8) the composition of the above (1), wherein the compound having angiotensin II antagonistic activity is 1-(cyclohexyloxycarbonyloxy)ethyl 2-ethoxy-1-[[2'-(1H-tetrazol-5-yl)biphenyl-4-yl]methyl]benzimidazole-7-carboxylate;

(9) the composition of the above (1), wherein the compound having angiotensin II antagonistic activity is 2-ethoxy-1-[[2'-(2,5-dihydro-5-oxo-1,2,4-oxadiazol-3-yl)biphenyl-4-yl]methyl]benzimidazole-7-carboxylic acid; and

(10) the composition of the above (1), which is an agent for improving a retinal potential or retinal edema.

In the present specification, the angiotensin II antagonistic activity is to inhibit competitively or non-competitively binding of angiotensin II to the angiotensin II receptors on the cellular membrane so as to reduce potent vasoconstrictive action or vascular smooth muscle proliferation action induced by angiotensin II and to ameliorate the symptom of hypertension.

The compound having angiotensin II antagonistic activity to be used for the present invention may be either a peptide compound or a non-peptide compound. In view of the advantage of long action, a non-peptide compound having angiotensin II antagonistic activity is preferable. As the compound having angiotensin II antagonistic activity, a compound having an oxygen atom in its molecule is preferable, a compound having an ether linkage or a carbonyl group (said carbonyl group may form a hydroxyl group by resonance) is more preferable, a compound having an ether linkage or a ketone derivative is further preferable, and in particular, an ether derivative is preferable.

Any non-peptide compound having angiotensin II antagonistic activity can be used for the present invention. Examples of said compounds include imidazole derivatives disclosed in Japanese Patent Unexamined Publication No. 71073/1981, Japanese Patent Unexamined Publication No. 71074/1981, Japanese Patent Unexamined Publication No. 98270/1982, Japanese Patent Unexamined Publication No. 157768/1983, U.S. Pat. No. 4,355,040, U.S. Pat. No. 4,340, 598, etc.; modified imidazole derivatives disclosed in EP-253310, EP-291969, EP-324377, EP-403158, WO-9100277, Japanese Patent Unexamined Publication No. 23868/1988, Japanese Patent Unexamined Publication No. 117876/1989, etc.; pyrrole, pyrazole and triazole derivatives disclosed in U.S. Pat. No. 5,183,899, EP-323841, EP-409332, Japanese Patent Unexamined Publication No. 287071/1989, in etc.; benzimidazole derivatives disclosed in U.S. Pat. No. 4,880,804, EP-0392317, EP-0399732, EP-0400835, EP-425921, EP-459136, Japanese Patent Unexamined Publication No. 63264/1991, etc.; azaindene derivatives disclosed in EP-399731, etc.; pyrimidone derivatives disclosed in EP-407342, etc.; quinazoline derivatives disclosed in EP-411766, etc.; xanthine derivatives disclosed in EP-430300, etc.; fused imidazole derivatives disclosed in EP-434038, etc.; pyrimidinedione derivatives disclosed in EP-442473, etc.; thienopyridone derivatives disclosed in EP-443568, etc.; heterocyclic compounds disclosed in EP-445811, EP-483683, EP-518033, EP-520423, EP-588299, EP-603712, etc. In addition, their representative compounds are described in Journal of Medicinal Chemistry, Vol. 39, No. 3, pages 625–656 (1996). As the non-peptide compound having angiotensin II antagonistic activity, any one in addition to the compounds described in the above-mentioned references can be employed as far as it has angiotensin II antagonistic activity. Among others, Losartan (DuP753), Eprosartan (SK&F108566), Candesartan cilexetil (TCV-116), Valsartan (CGP-48933), Telmisartan (BIBR277), Irbesartan (SR47436), Tasosartan (ANA-756), their active metabolites (Candesartan, etc.), etc. are preferable.

Preferred examples of the non-peptide compound having angiotensin II antagonistic activity include, for example, a benzimidazole derivative of the formula (I):

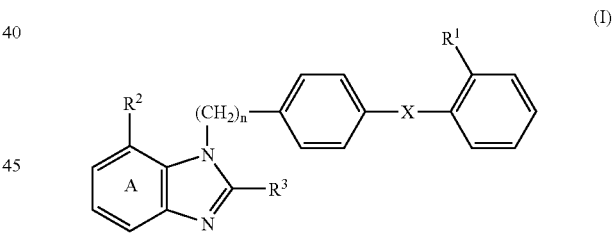

wherein R¹ is a group capable of forming an anion or a group capable of converting thereinto, X shows that the phenylene group and the phenyl group bind to each other directly or through a spacer having an atomic chain length of 2 or less, n is an integer of 1 or 2, the ring A is a benzene ring having an optional substitution, in addition to the group R², R² is a group capable of forming an anion or a group capable of converting thereinto, and R³ is an optionally substituted hydrocarbon residue which may bind through a hetero-atom (preferably, an optionally substituted hydrocarbon residue which binds through an oxygen atom), etc., or a salt thereof.

In the above formula (I), the group capable of forming an anion (a group having a hydrogen atom capable of leaving as a proton) as R¹ include, for example, (1) a carboxyl group, (2) a tetrazolyl group, (3) a trifluoromethanesulfonic acid amido group (—NHSO₂CF₃), (4) a phosphono group, (5) a sulfo group, (6) an optionally substituted 5- to 7-membered (preferably 5- to 6-membered) monocyclic heterocyclic ring residue which contains one or more of N, S and O, etc.

Examples of the above "optionally substituted 5- to 7-membered (preferably 5- to 6-membered) monocyclic heterocyclic ring residue which contains one or more of N, S and O" include

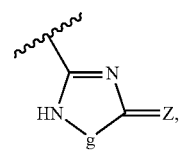
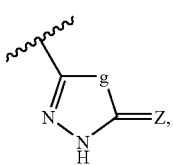
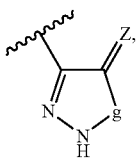
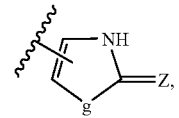
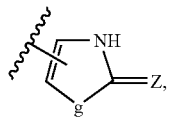
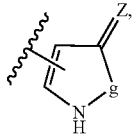
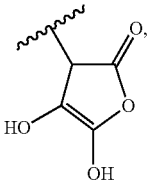
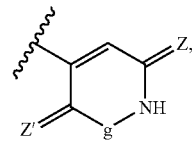

-continued

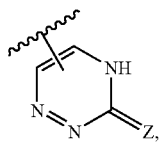
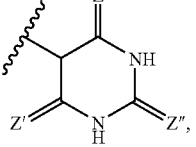
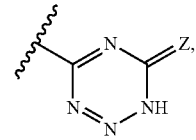
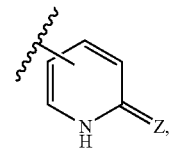
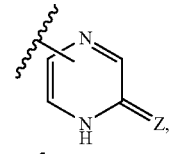
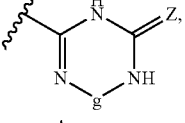
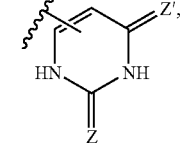
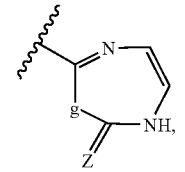
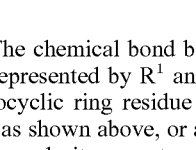

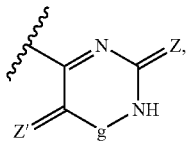
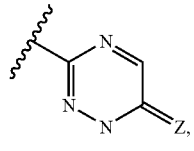
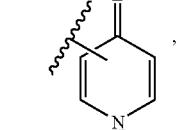
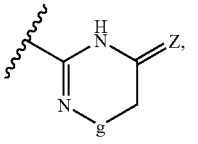
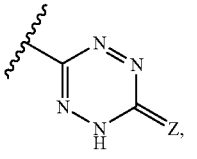
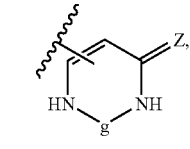
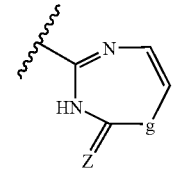
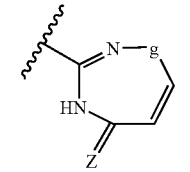

etc. The chemical bond between the heterocyclic ring residue represented by $R^1$ and the phenyl group to which said heterocyclic ring residue binds may be a carbon—carbon bond as shown above, or a nitrogen-carbon bond via one of the several nitrogen atoms when the symbol g is —NH—, etc. in the above formulas.

For example, when $R^1$ is represented by the formula:

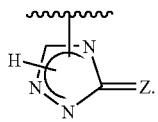

its specific embodiments are

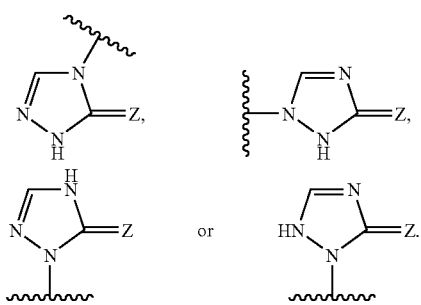

her examples of $R^1$ binding through a nitrogen atom include

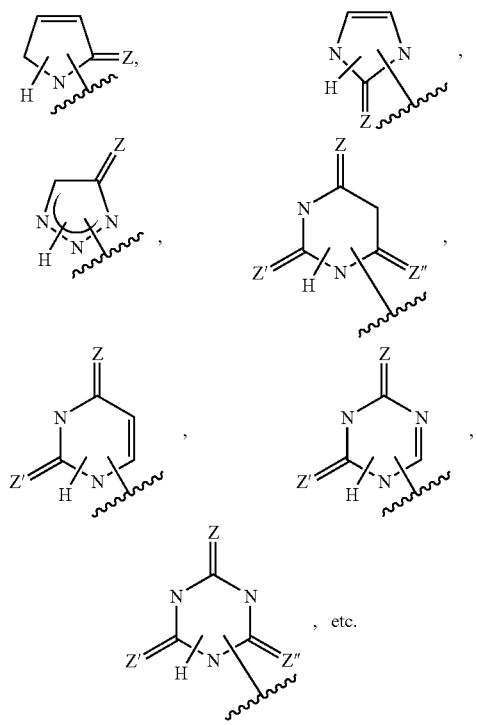

In the above formula, g is —$CH_2$—, —NH—, —O— or —$S(O)m$—; >=Z, >=Z' and >=Z" are independently a carbonyl group, a thiocarbonyl group or an optionally oxidized sulfur atom (e.g., S, S(O), $S(O)_2$, etc.) (preferably a carbonyl group or a thiocarbonyl group, more preferably carbonyl group); and m is an integer of 0, 1 or 2.

Preferred examples of the heterocyclic ring residue represented by $R^1$ include a heterocyclic ring residue simultaneously having —NH— or —OH group as proton donor and a carbonyl group, a thiocarbonyl group, a sulfinyl group, etc. as proton acceptor, such as an oxadiazolone ring, an oxadiazolothione ring or an thiadiazolone ring, etc.

While the heterocyclic ring residue represented by $R^1$ may form a condensed ring by connecting the substituents on the heterocyclic ring, it is preferably 5- to 6-membered ring residue, more preferably 5-membered ring residue.

Preferred examples of the heterocyclic ring residue represented by $R^1$ include a group of the formula:

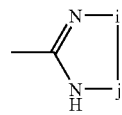

wherein i is —O— or —S—, j is >=O, >=S or >=S(O)m, and m is as defined above (preferably, 2,5-dihydro-5-oxo-1,2,4-oxadiazol-3-yl, 2,5-dihydro-5-thioxo-1,2,4-oxadiazol-3-yl, 2,5-dihydro-5-oxo-1,2,4-thiadiazol-3-yl; more preferably, 2,5-dihydro-5-oxo-1,2,4-oxadiazol-3-yl).

The above-mentioned heterocyclic ring residue ($R^1$) have the following tautomeric isomers. For example, in

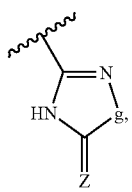

when Z is 0 and g is 0,

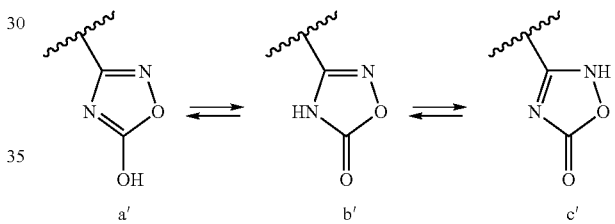

the three tautomeric isomers a', b' and c' exist and a group of the formula:

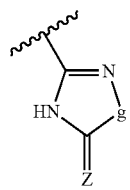

include all of the above a', b' and c'.

The group capable of forming an anion as $R^1$ may be protected by an optionally substituted lower ($C_{1-4}$) alkyl group, an acyl group (e.g., lower ($C_{2-5}$) alkanoyl, benzoyl, etc.), etc. at its possible position.

Examples of the optionally substituted lower ($C_{1-4}$) alkyl group include (1) a lower ($C_{1-4}$) alkyl group optionally substituted with one to three phenyl groups which may have halogen atom, nitro, lower ($C_{1-4}$) alkyl, lower ($C_{1-4}$) alkoxy, etc. (e.g., methyl, triphenylmethyl, p-methoxybenzyl, p-nitrobenzyl, etc.); (2) a lower ($C_{1-4}$) alkoxy-lower ($C_{1-4}$) alkyl group (e.g., methoxymethyl, ethoxymethyl, etc.); (3) a group of the formula: —CH($R^4$)—OCO$R^5$ wherein $R^4$ is (a) a hydrogen, (b) a straight or branched lower $C_{1-6}$ alkyl group (e.g., methyl, ethyl, n-propyl, isopropyl, n-butyl, isobutyl, t-butyl, n-pentyl, isopentyl, neopentyl, etc.), (c) a straight or branched lower $C_{2-6}$ alkenyl group or (d) a $C_{3-8}$ cycloalkyl group (e.g., cyclopentyl, cyclohexyl, cycloheptyl, etc.), and $R^5$ is (a) a straight or branched lower $C_{1-6}$ alkyl group (e.g., methyl, ethyl, n-propyl, isopropyl, n-butyl, isobutyl, sec-butyl, t-butyl, n-pentyl, isopentyl, neopentyl, etc.), (b) a straight or branched lower $C_{2-6}$ alkenyl group, (c) a lower $C_{1-3}$ alkyl group substituted with a $C_{3-8}$ cycloalkyl group (e.g., cyclopentyl, cyclohexyl, cycloheptyl, etc.) or an optionally substituted aryl group (e.g., a phenyl group, a naphthyl group, etc., optionally having a halogen atom, a nitro, a lower ($C_{1-4}$) alkyl, a lower ($C_{1-4}$) alkoxy, etc.) such as benzyl, p-chlorobenzyl, phenethyl, cyclopentylmethyl, cyclohexylmethyl, etc., (d) a lower $C_{2-3}$ alkenyl group substituted with a $C_{3-8}$ cycloalkyl or an optionally substituted aryl group (e.g., a phenyl group, a naphthyl group, etc., optionally having a halogen atom, a nitro, a lower ($C_{1-4}$) alkyl, a lower ($C_{1-4}$) alkoxy, etc.) such as cinnamyl, etc. having an alkenyl moiety such as vinyl, propenyl, allyl, isopropenyl, etc., (e) an optionally substituted aryl group (e.g., a phenyl group, a naphthyl group, etc., optionally having a halogen atom, a nitro, a lower ($C_{1-4}$) alkyl, a lower ($C_{1-4}$) alkoxy, etc.) such as phenyl, p-tolyl, naphthyl, etc., (f) a straight or branched lower $C_{1-6}$ alkoxy group (e.g., methoxy, ethoxy, n-propoxy, isopropoxy, n-butoxy, isobutoxy, sec-butoxy, t-butoxy, n-pentyloxy, isopentyloxy, neopentyloxy, etc.), (g) a straight or branched lower $C_{2-8}$ alkenyloxy group (e.g., allyloxy, isobutenyloxy, etc.), (h) a $C_{3-8}$ cycloalkyloxy group (e.g., cyclopentyloxy, cyclohexyloxy, cycloheptyloxy, etc.), (i) a lower $C_{1-3}$ alkoxy group substituted with a $C_{3-8}$ cycloalkyl (e.g., cyclopentyl, cyclohexyl, cycloheptyl, etc.) or an optionally substituted aryl group (e.g., a phenyl group, a naphthyl group, etc., optionally having a halogen atom, a nitro, a lower ($C_{1-4}$) alkyl, a lower ($C_{1-4}$) alkoxy, etc.) such as benzyloxy, phenethyloxy, cyclopentylmethoxy, cyclohexylmethoxy, etc. having an alkoxy moiety such as methoxy, ethoxy, n-propoxy, isopropoxy, etc., etc.), (j) a lower $C_{2-3}$ alkenyloxy group substituted with a $C_{3-8}$ cycloalkyl (e.g., cyclopentyl, cyclohexyl, cycloheptyl, etc.) or an optionally substituted aryl group (e.g., a phenyl group or a naphthyl group, etc., optionally having a halogen atom, a nitro, a lower ($C_{1-4}$) alkyl, a lower ($C_{1-4}$) alkoxy, etc.) such as cinnamyloxy, etc. having an alkenyloxy moiety such as vinyloxy, propenyloxy, allyloxy, isopropenyloxy, etc. or (k) an optionally substituted aryloxy group (e.g., a phenoxy group, a naphthoxy group, etc., optionally having a halogen atom, a nitro, a lower ($C_{1-4}$) alkyl, a lower ($C_{1-4}$) alkoxy, etc.) such as phenoxy, p-nitrophenoxy, naphthoxy, etc.; etc.

The group capable of forming an anion as $R^1$ may be substituted, in addition to the above protective group such as an optionally substituted lower ($C_{1-4}$) alkyl group or an acyl group (e.g., lower ($C_{2-5}$) alkanoyl, benzoyl, etc.), etc., with an optionally substituted lower ($C_{1-4}$) alkyl group (e.g. an optionally substituted lower ($C_{1-4}$) alkyl group similar to the "optionally substituted lower ($C_{1-4}$) alkyl group" exemplified as a protective group for the above group capable of forming an anion as $R^1$), a halogen atom, a nitro, a cyano, a lower ($C_{1-4}$) alkoxy, an amino optionally substituted with 1 to 2 lower ($C_{1-4}$) alkyl groups, etc., at the possible position.

In the above formula, the group convertible into the group capable of forming an anion (a group having a hydrogen atom capable of leaving as proton) as $R^1$ may be a group convertible into a group capable of forming an anion under biological or physiological conditions (for example, in vivo reaction, etc. such as oxidation, reduction, hydrolysis, etc. by in vivo enzyme, etc.) [so called pro-drug], or the group convertible into a group capable of forming an anion represented by $R^1$ may be a group chemically convertible into a group capable of forming an anion, such as cyano, N-hydroxycarbamimidoyl group (—C(=N—OH)—NH$_2$), a group selected from the class consisting of (1) a carboxyl group, (2) a tetrazolyl group, (3) a trifluoromethanesulfonic acid amido group (—NHSO$_2$CF$_3$), (4) a phosphono group, (5) a sulfo group and (6) an optionally substituted monocyclic 5- to 7-membered (preferably 5- to 6-membered) monocyclic heterocyclic ring residue which contains one or more of N, S and O, each of which is protected with an optionally substituted lower ($C_{1-4}$) alkyl group or an acyl group, etc. [so called synthetic intermediate].

As the group $R^1$, carboxyl, tetrazolyl or 4,5-dihydro-5-oxo-1,2,4-oxadiazol-3-yl (preferably, tetrazolyl), each of which may be protected with an optionally substituted lower ($C_{1-4}$) alkyl (e.g., methyl, triphenylmethyl, methoxymethyl, ethoxymethyl, p-methoxybenzyl, p-nitrobenzyl, etc.) or an acyl group (e.g., lower ($C_{2-5}$) alkanoyl, benzoyl, etc.); or cyano or N-hydroxycarbamimidoyl (preferably cyano) is preferable. Among others, cyano is preferable.

In the above formula, X shows that the phenylene group is bonded to the adjacent phenyl group directly or through a spacer with an atomic chain of 2 or less (preferably directly). Examples of the spacer with an atomic chain of 2 or less include any divalent chain in which the number of atoms constituting the straight chain is 1 or 2 and which may have a side chain, and specifically lower ($C_{1-4}$) alkylene in which the number of atoms constituting the straight chain is 1 or 2, —CO—, —O—, —S—, —NH—, —CO—NH—, —O—CH$_2$—, —S—CH$_2$—, —CH=CH—, etc.

In the above formula, n is an integer of 1 or 2 (preferably 1).

In the above formula, the ring A may have, in addition to the group $R^2$, another substituent, for example, (1) halogen (e.g., F, Cl, Br, etc.), (2) cyano, (3) nitro, (4) an optionally substituted lower ($C_{1-4}$) alkyl, (5) a lower ($C_{1-4}$) alkoxy, (6) an optionally substituted amino group (e.g., amino, N-lower ($C_{1-4}$) alkylamino (e.g., methylamino, etc.), N,N-di-lower ($C_{1-4}$) alkylamino (e.g., dimethylamino, etc.), N-arylamino (e.g., phenylamino, etc.), alicyclic amino (e.g., morpholino, piperidino, piperazino, N-phenylpiperazino, etc.), etc.), (7) a group of the formula: —CO—D' wherein D' is a hydroxyl group or a lower ($C_{1-4}$) alkoxy whose alkyl moiety may be substituted with a hydroxyl group, a lower ($C_{1-4}$) alkoxy, a lower ($C_{2-6}$) alkanoyloxy (e.g., acetoxy, pivaloyloxy, etc.), a lower ($C_{1-6}$) alkoxy-carbonyloxy (e.g., methoxycarbonyloxy, ethoxycarbonyloxy, etc.) or a lower ($C_{3-6}$) cycloalkoxycarbonyloxy (e.g., cyclohexyloxycarbonyloxy, etc.), or (8) tetrazolyl, trifluoromethanesulfonic acid amide group, phosphono group or sulfo group, each of which may be protected with an optionally substituted lower ($C_{1-4}$) alkyl ("an optionally substituted lower ($C_{1-4}$) alkyl group" similar to that exemplified as a protective group for the above group capable of forming an anion represented by $R^1$, etc.) or acyl (e.g., lower ($C_{2-5}$) alkanoyl, benzoyl, etc.), etc.

Of these substituents, one or two may simultaneously be present at any possible position on the benzene ring, in addition to the group $R^2$, and preferred examples of the substituents for the benzene ring represented by A include an optionally substituted lower ($C_{1-4}$) alkyl (e.g., a lower ($C_{1-4}$) alkyl, etc. optionally substituted with a hydroxyl group, a carboxyl group, a halogen, etc.), a halogen, etc. As the ring A, a benzene ring having no substituent in addition to the group $R^2$ is preferable.

In the above formula, examples of the group capable of forming an anion (a group having a hydrogen atom capable of leaving as proton) as $R^2$ include (1) an optionally esterified or amidated carboxyl group, (2) a tetrazolyl group, (3) a trifluoromethanesulfonic acid amido group ($-NHSO_2CF_3$), (4) a phosphono group, (5) a sulfo group, etc., each of which may be protected with an optionally substituted lower alkyl group (e.g. an optionally substituted lower ($C_{1-4}$) alkyl group similar to the "optionally substituted lower ($C_{1-4}$) alkyl group" exemplified as a protective group for the above group capable of forming an anion as $R^1$) or an acyl group (e.g., lower ($C_{2-5}$) alkanoyl, benzoyl, etc.), or any one of the groups capable of converting thereinto under biological or physiological conditions (for example, in vivo reaction, etc. such as oxidation, reduction, hydrolysis, etc. by in vivo enzyme, etc.), or chemically.

Examples of the optionally esterified or amidated carboxyl as $R^2$ include a group of the formula: $-CO-D$ wherein D is (1) a hydroxyl group, (2) an optionally substituted amino (for example, amino, N-lower ($C_{1-4}$) alkylamino, N,N-di-lower ($C_{1-4}$) alkylamino, etc.) or (3) an optionally substituted alkoxy (e.g., (i) a lower ($C_{1-6}$) alkoxy group whose alkyl moiety is optionally substituted with a hydroxyl group, an optionally substituted amino (e.g., amino, N-lower ($C_{1-4}$) alkylamino, N,N-di-lower ($C_{1-4}$) alkylamino, piperidino, morpholino, etc.), a halogen, a lower ($C_{1-6}$) alkoxy, a lower ($C_{1-6}$) alkylthio, a lower ($C_{3-8}$) cycloalkoxy or an optionally substituted dioxolenyl (e.g., 5-methyl-2-oxo-1,3-dioxolen-4-yl, etc.), or (ii) a group of the formula: $-O-CH(R^6)-OCOR^7$ wherein $R^6$ is (a) a hydrogen, (b) a straight or branched $C_{1-6}$ lower alkyl group (e.g., methyl, ethyl, n-propyl, isopropyl, n-butyl, isobutyl, t-butyl, n-pentyl, isopentyl, neopentyl, etc.), (c) a straight or branched $C_{2-6}$ lower alkenyl group or (d) a $C_{3-8}$ cycloalkyl group (e.g., cyclopentyl, cyclohexyl, cycloheptyl, etc.), and $R^7$ is (a) a straight or branched $C_{1-6}$ lower alkyl group (e.g., methyl, ethyl, n-propyl, isopropyl, n-butyl, isobutyl, sec-butyl, t-butyl, n-pentyl, isopentyl, neopentyl, etc.), (b) a straight or branched $C_{2-6}$ lower alkenyl group, (c) a lower $C_{1-3}$ alkyl group substituted with a $C_{3-8}$ cycloalkyl group (e.g., cyclopentyl, cyclohexyl, cycloheptyl, etc.) or an optionally substituted aryl group (e.g., a phenyl group, a naphthyl group, etc., optionally having a halogen atom, a nitro, a lower ($C_{1-4}$) alkyl, a lower ($C_{1-4}$) alkoxy, etc.) such as benzyl, p-chlorobenzyl, phenethyl, cyclopentylmethyl, cyclohexylmethyl, etc., (d) a lower $C_{2-3}$ alkenyl group substituted with a $C_{3-8}$ cycloalkyl or an optionally substituted aryl group (e.g., a phenyl group, a naphthyl group, etc., optionally having a halogen atom, a nitro, a lower ($C_{1-4}$) alkyl, a lower ($C_{1-4}$) alkoxy, etc.) such as cinnamyl, etc. having an alkenyl moiety such as vinyl, propenyl, allyl, isopropenyl, etc., (e) an optionally substituted aryl group (e.g., a phenyl group, a naphthyl group, etc., optionally having a halogen atom, a nitro, a lower ($C_{1-4}$) alkyl, a lower ($C_{1-4}$) alkoxy, etc.) such as phenyl, p-tolyl, naphthyl, etc., (f) a straight or branched lower $C_{1-6}$ alkoxy group (e.g., methoxy, ethoxy, n-propoxy, isopropoxy, n-butoxy, isobutoxy, sec-butoxy, t-butoxy, n-pentyloxy, isopentyloxy, neopentyloxy, etc.), (g) a straight or branched lower $C_{2-8}$ alkenyloxy group (e.g., allyloxy, isobutenyloxy, etc.), (h) a $C_{3-8}$ cycloalkyloxy group (e.g., cyclopentyloxy, cyclohexyloxy, cycloheptyloxy, etc.), (i) a lower $C_{1-3}$ alkoxy group substituted with a $C_{3-8}$ cycloalkyl (e.g., cyclopentyl, cyclohexyl, cycloheptyl, etc.) or an optionally substituted aryl group (e.g., a phenyl group, a naphthyl group, etc., optionally having a halogen atom, a nitro, a lower ($C_{1-4}$) alkyl, a lower ($C_{1-4}$) alkoxy, etc.) such as benzyloxy, phenethyloxy, cyclopentylmethoxy, cyclohexylmethoxy, etc. having an alkoxy moiety such as methoxy, ethoxy, n-propoxy, isopropoxy, etc., etc.), (j) a lower $C_{2-3}$ alkenyloxy group substituted with a $C_{3-8}$ cycloalkyl (e.g., cyclopentyl, cyclohexyl, cycloheptyl, etc.) or an optionally substituted aryl group (e.g., a phenyl group or a naphthyl group, etc., optionally having a halogen atom, a nitro, a lower ($C_{1-4}$) alkyl, a lower ($C_{1-4}$) alkoxy, etc.) such as cinnamyloxy, etc. having an alkenyloxy moiety such as vinyloxy, propenyloxy, allyloxy, isopropenyloxy, etc. or (k) an optionally substituted aryloxy group (e.g., a phenoxy group, a naphthoxy group, etc., optionally having a halogen atom, a nitro, a lower ($C_{1-4}$) alkyl, a lower ($C_{1-4}$) alkoxy, etc.) such as phenoxy, p-nitrophenoxy, naphthoxy, etc.], etc.

As $R^2$, an optionally esterified carboxyl is preferable, and its specific examples include $-COOH$ and a salt thereof, $-COOMe$, $-COOEt$, $-COOtBu$, $-COOPr$, pivaloyloxymethoxy-carbonyl, 1-(cyclohexyloxycarbonyloxy)ethoxycarbonyl, 5-methyl-2-oxo-1,3-dioxolen-4-yl-methoxycarbonyl, acetoxymethoxycarbonyl, propionyloxymethoxycarbonyl, n-butyryloxymethoxycarbonyl, isobutyryloxymethoxycarbonyl, 1-(ethoxycarbonyloxy)ethoxycarbonyl, 1-(acetoxy)-ethoxycarbonyl, 1-(isobutyryloxy)ethoxycarbonyl, cyclohexylcarbonyloxymethoxycarbonyl, benzoyloxy-methoxycarbonyl, cinnamyloxycarbonyl, cyclopentyl-carbonyloxymethoxycarbonyl, etc. The group $R^2$ may be any one of the groups capable of forming an anion under biological or physiological conditions (for example, in vivo reaction, etc. such as oxidation, reduction, hydrolysis, etc. by in vivo enzyme, etc.), the groups capable of chemically forming an anion (e.g., $COO-$, its derivative, etc.) or the groups capable of converting thereinto. The group $R^2$ may be a carboxyl group or its pro-drug.

Preferred examples of the group $R^2$ include a group of the formula: $-CO-D$ wherein D is (1) a hydroxyl group or (2) a lower ($C_{1-4}$) alkoxy whose alkyl moiety is optionally substituted with a hydroxyl group, an amino, a halogen, a lower ($C_{2-6}$) alkanoyloxy (e.g., acetoxy, pivaloyloxy, etc.), a lower ($C_{3-8}$) cycloalkanoyloxy, a lower ($C_{1-6}$) alkoxy-carbonyloxy (e.g., methoxycarbonyloxy, ethoxycarbonyloxy, etc.), a lower ($C_{3-8}$) cycloalkoxycarbonyloxy (e.g., cyclohexyloxycarbonyloxy, etc.), a lower ($C_{1-4}$) alkoxy or a lower ($C_{3-8}$) cycloalkoxy. Among others, an esterified carboxyl with a lower ($C_{1-4}$) alkyl (preferably, methyl or ethyl) is preferable.

In the above formula, examples of the "hydrocarbon residue" in the "optionally substituted hydrocarbon residue which may bind through a hetero-atom" represented by $R^3$ include (1) an alkyl group, (2) an alkenyl group, (3) an alkynyl group, (4) an cycloalkyl group, (5) an aryl group, (6) an aralkyl group, etc. Among others, an alkyl group, an alkenyl group and a cycloalkyl group are preferable.

Examples of the alkyl group of the above mentioned (1) include straight or branched lower alkyl group having about 1–8 carbon atoms such as methyl, ethyl, propyl, isopropyl, butyl, isobutyl, sec-butyl, t-butyl, pentyl, i-pentyl, hexyl, heptyl, octyl, etc.

Examples of the alkenyl group of the above mentioned (2) include straight or branched lower alkenyl group having about 2–8 carbon atoms such as vinyl, propenyl, 2-butenyl, 3-butenyl, isobutenyl, 2-octenyl, etc.

Examples of the alkynyl group of the above mentioned (3) include straight or branched lower alkynyl group having about 2–8 carbon atoms such as ethynyl, 2-propynyl, 2-butynyl, 2-pantynyl, 2-octynyl, etc.

Examples of the cycloalkyl group of the above (4) include a lower cycloalkyl having about 3–6 carbon atoms, such as cyclopropyl, cyclobutyl, cyclopentyl, cyclohexyl, etc.

Each of the above-mentioned alkyl group, alkenyl group, alkynyl group and cycloalkyl group may be substituted with hydroxyl group, an optionally substituted amino group (e.g., amino, N-lower ($C_{1-4}$) alkylamino, N,N-di-lower ($C_{1-4}$) alkylamino, etc.), halogen, lower ($C_{1-4}$) alkoxy group, lower ($C_{1-4}$) alkylthio group, etc.

Examples of the aralkyl group of the above (5) include a phenyl-lower ($C_{1-4}$) alkyl, etc., such as benzyl, phenethyl, etc.

Examples of the aryl group of the above (6) include phenyl, etc.

Each of the above-mentioned aralkyl group and aryl group may be substituted, at any possible position on the benzene ring, with a halogen (e.g., F, Cl, Br, etc.), a nitro, an optionally substituted amino group (e.g., amino, N-lower ($C_{1-4}$) alkylamino, N,N-di-lower ($C_{1-4}$) alkylamino, etc.), a lower ($C_{1-4}$) alkoxy (e.g., methoxy, ethoxy, etc.), a lower ($C_{1-4}$) alkylthio (e.g., methylthio, ethylthio, etc.), a lower ($C_{1-4}$) alkyl (e.g., methyl, ethyl, etc.), etc.

Preferred examples of the "optionally substituted hydrocarbon residue" in the "optionally substituted hydrocarbon residue which may bind through a hetero-atom" represented by $R^3$ include an optionally substituted alkyl or alkenyl group (e.g., a lower ($C_{1-5}$) alkyl or a lower ($C_{2-5}$) alkenyl group, each of which may be substituted with a hydroxyl group, an amino group, a halogen, a lower ($C_{1-4}$) alkoxy group, etc.). Among others, a lower ($C_{1-5}$) alkyl (more preferably, ethyl) is preferable.

Preferred examples of the "hetero-atom" in the "optionally substituted hydrocarbon residue which may bind through a hetero-atom" represented by $R^3$ include —O—, —S(O)m- [m is an integer of 0–2], —NR'— [R' is a hydrogen atom or a lower ($C_{1-4}$) alkyl], etc. Among others, —O— is preferable.

Among others, as $R^3$, a lower ($C_{1-5}$) alkyl or a lower ($C_{2-5}$) alkenyl group, each of which may be substituted with a substituent selected from the class consisting of a hydroxyl group, an amino group, a halogen and a lower ($C_{1-4}$) alkoxy group and which may bind through —O—, —S(O)m- [m is an integer of 0–2] or —NR'— [R' is a hydrogen atom or a lower ($C_{1-4}$) alkyl], etc. is preferable and a lower ($C_{1-5}$) alkyl or lower ($C_{1-5}$) alkoxy (in particular, ethoxy) is more preferable.

Among the compounds having angiotensin II antagonistic activity and represented by the formula (I), a benzimidazole-7-carboxylic acid derivative of the formula (I'):

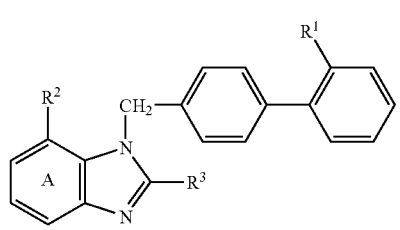

(I')

wherein $R^1$ is (1) carboxyl group, (2) tetrazolyl group or (3) a group of the formula:

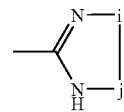

wherein i is —O— or —S—, j is >=O, >=S or >=S(O)m, and m is as defined above; the ring A is a benzene ring having an optional substituent selected from the class consisting of an optionally substituted lower ($C_{1-4}$) alkyl (e.g., a lower ($C_{1-4}$) alkyl optionally substituted with a hydroxyl group, a carboxyl group, a halogen, etc.) and a halogen, in addition to the group $R^2$ (preferably, a benzene ring having no substituent in addition to the group $R^2$); $R^2$ is a group of the formula: —CO-D wherein D is (1) a hydroxyl group or (2) a lower ($C_{1-4}$) alkoxy whose alkyl moiety may be substituted with a hydroxyl group, an amino, a halogen, a lower ($C_{2-6}$) alkanoyloxy (e.g., acetoxy, pivaloyloxy, etc.), a lower ($C_{3-8}$) cycloalkanoyloxy, a lower ($C_{1-6}$) alkoxycarbonyloxy (e.g., methoxycarbonyloxy, ethoxy-carbonyloxy, etc.), a lower ($C_{3-8}$) cycloalkoxycarbonyloxy. (e.g., cyclohexyloxycarbonyloxy, etc.), a lower ($C_{1-4}$) alkoxy or a lower ($C_{3-8}$) cycloalkoxy; $R^3$ is a lower ($C^{1-5}$) alkyl or a lower ($C_{2-5}$) alkenyl group, each of which may bind through O—, —S(O)m- [m is an integer of 0–2] or —NR'— [R' is a hydrogen atom or a lower ($C_{1-4}$) alkyl] and which may be substituted with a substituent selected from the class consisting of a hydroxyl group, an amino group, a halogen and a lower ($C_{1-4}$) alkoxy group (preferably, a lower ($C_{1-5}$) alkyl or a lower ($C_{1-5}$) alkoxy; more preferably, ethoxy), etc. or a pharmaceutically acceptable salt thereof is preferable.

Among others, 2-ethoxy-1-[[2'-(1H-tetrazol-5-yl)biphenyl-4-yl]methyl]benzimidazole-7-carboxylic acid [Candesartan], 1-(cyclohexyloxycarbonyloxy)ethyl 2-ethoxy-1-[[2'-(1H-tetrazol-5-yl)biphenyl-4-yl]methyl]-benzimidazole-7-carboxylate [Candesartan cilexetil], pivaloyloxymethyl 2-ethoxy-1-[[2'-(1H-tetrazol-5-yl)biphenyl-4-yl]methyl]benzimidazole-7-carboxylate, 2-ethoxy-1-[[2'-(2,5-dihydro-5-oxo-1,2,4-oxadiazol-3-yl)biphenyl-4-yl]methyl]benzimidazole-7-carboxylic acid, etc. or a salt thereof are preferable.

The above mentioned benzimidazole derivative can be produced by known methods described in, for example, EP-425921, EP-459136, EP-553879, EP-578125, EP-520423, EP-668272, etc. or a method analogous thereto. When Candesartan cilexetil is used for the present invention, a stable C-type crystal described in EP-459136 is preferably used.

The compound having angiotensin II antagonistic activity or a pro-drug thereof may be distinct entity or in the form of any possible pharmaceutically acceptable salts thereof. Examples of said salts include a salt with inorganic bases (e.g., alkaline metals such as sodium, potassium, etc.; alkaline earth metals such as calcium, magnesium, etc.; transition metal such as zinc, iron, copper, etc.; etc.); organic bases (e.g., organic amines such as trimethylamine, triethylamine, pyridine, picoline, ethanolamine, diethanolamine, triethanolamine, dicyclohexylamine, N,N'-dibenzylethylenediamine, etc.; basic amino acids such as arginine, lysine, ornithine, etc.; etc.); etc., when said compound having angiotensin II antagonistic activity has an acidic group such as a carboxyl group, etc.; and a salt with inorganic acids or organic acids (e.g., hydrochloric acid, nitric acid, sulfuric acid, phosphoric acid, carbonic acid, bicarbonic acid, formic acid, acetic acid, propionic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.); acidic amino acids such as aspartic acid, glutamic acid, etc.; etc., when said compound having angiotensin II antagonistic activity has a basic group such as an amino group, etc.

The pro-drug of the compound having angiotensin II antagonistic activity [hereinafter, referred to as AII antagonist] means a compound which is converted to AII antagonist under the physiological condition or with a reaction due to an enzyme, an gastric acid, etc. in the living body, that is, a compound which is converted to AII antagonist with oxidation, reduction, hydrolysis, etc. according to an enzyme; a compound which is converted to AII antagonist with gastric acid, etc.; etc.

Examples of the pro-drug of the AII antagonist include a compound wherein an amino group of the AII antagonist is substituted with acyl, alkyl, phosphoric acid, etc. (e.g. a compound wherein an amino group of the AII antagonist is substituted with eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl, tert-butyl, etc.); a compound wherein an hydroxyl group of the AII antagonist is substituted with acyl, alkyl, phosphoric acid, boric acid, etc. (e.g. a compound wherein an hydroxyl group of the AII antagonist is substituted with acetyl, palmitoyl, propanoyl, pivaloyl, succinyl, fumaryl, alanyl, dimethylaminomethylcarbonyl, etc.); a compound wherein a carboxyl group of the AII antagonist is modified with ester, amide, etc. (e.g. a compound wherein a carboxyl group of the AII antagonist is modified with ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester, methyl amide, etc.); etc. These pro-drug can be produced by per se known method from the AII antagonist.

The pro-drug of the AII antagonist may be a compound which is converted into the AII antagonist under the physiological conditions as described in "Pharmaceutical Research and Development", Vol. 7 (Drug Design), pages 163-198 published in 1990 by Hirokawa Publishing Co. (Tokyo, Japan).

Also, the AII antagonist may be hydrated.

The compound having angiotensin II antagonistic activity or prodrug thereof, or a salt thereof [preferably, compounds of the formula (I) and their pharmaceutically acceptable salt] is low in toxicity and can be administered as it is, or as a pharmaceutical composition thereof with a pharmaceutically acceptable carrier, to mammals (e.g., men, mice, rats, rabbits, dogs, cats, bovines, pigs, monkeys, etc.) so as to prevent, treat or development-inhibit simple retinopathy or preproliferative retinopathy.

Here, examples of the carriers include various organic or inorganic carriers which are generally used in this field. For example, an excipient, a lubricant, a binder, an disintegrating agent, etc. are used in the solid formulations, and a solvent, a solubilizer, a suspending agent, a isotonizing agent, a buffer, a soothing agent, etc. are used in the liquid formulations. In addition, if desired, an appropriate additive such as a preservative, an antioxidant, a colorant, a sweetener, etc. may be used in the above formulations.

Examples of the excipient include lactose, sucrose, D-mannitol, D-sorbitol, starch, α-starch, dextrin, crystalline cellulose, hydroxypropyl cellulose with a low degree of substitution, sodium carboxymethyl cellulose, gum arabic, dextrin, pullulan, light silic acid anhydride, synthesized aluminum silicate, magnesium aluminate metasilicate, etc.

Examples of the lubricant include magnesium stearate, calcium stearate, talc, colloidal silica, etc.

Examples of the binder include α-starch, cane sugar, gelatin, gum arabic, methyl cellulose, carboxymethyl cellulose, sodium carboxymethyl cellulose, crystalline cellulose, sucrose, D-mannitol, trehalose, dextrin, pullulan, hydroxypropyl cellulose, hydroxypropylmethyl cellulose, polyvinyl-pyrrolidone, etc.

Examples of the disintegrating agent include lactose, sucrose, starch, carboxymethyl cellulose, carboxymethyl cellulose calcium, croscarmellose sodium, sodium carboxymethyl starch, light silic acid anhydride with a low degree of substitution, hydroxypropyl cellulose, etc.

Examples of the solvent include water for injection, Ringer solution, alcohol, propyleneglycol, polyethyleneglycol, sesame oil, corn oil, olive oil, cotton seed oil, etc.

Examples of the solubilizer include polyethyleneglycol, propyleneglycol, D-mannitol, trehalose, benzyl benzoate, ethanol, trisaminomethane, cholesterol, triethanolamine, sodium carbonate, sodium citrate, sodium salicylate, sodium acetate, etc.

Examples of the suspending agent include surfactants such as stearyl triethanolamine, sodium laurylsulfate, laurylaminopropionic acid, lecithin, benzalkonium chloride, benzetonium chloride, glycerin monostearate, etc.; hydrophilic polymers such as polyvinylalcohol, polyvinylpyrrolidone, sodium carboxymethyl cellulose, methyl cellulose, hydroxymethyl cellulose, hydroxyethyl cellulose, hydroxypropyl cellulose, etc.; polysorbates, polyoxyethylene hardened caster oil, etc.; etc.

Examples of the isotonizing agent include sodium chloride, glycerin, D-mannitol, D-sorbitol, glucose, etc.

Examples of the buffer include a buffer solution of phosphate, acetate, carbonate, citrate, etc.

Examples of the soothing agent include benzylalcohol, etc.

Examples of the preservative include paraoxybenzoic acid esters, chlorobutanol, benzylalcohol, phenethylalcohol, dehydroacetic acid, sorbic acid, etc.

Examples of the antioxidant include sulfites, ascorbic acid, etc.

Preferable examples of colorants include water-soluble synthetic organic food additives (e.g., food dyes such as food red dye Nos. 2 and 3, food yellow dye Nos. 4 and 5 and food blue dye Nos. 1 and 2), water-insoluble lake dyes (e.g., aluminum salts of the above water-soluble synthetic organic food additives, etc.), natural pigments (e.g., β-carotene, chlorophyll, iron oxide red, etc.), etc.

Preferable examples of edulcorants include sodium saccharate, glycyrrhizin dipotassium, aspartame, Stevia, etc.

The pharmaceutical composition is orally or parenterally administered in safety in the form of, for example, orally administered compositions such as tablets, capsules (including soft capsules and microcapsules), granules, powders, syrups, emulsions, suspensions, etc.; and parenterally administered compositions such as injections (e.g., subcutaneous injection, intravenous injection, intramuscular injection, intraperitoneal injection, intravitreous injection, injections to the eyeball and the retina, etc.), drops, medicines for external use (e.g., nasotracheally administered compositions, percutaneously administered compositions, ointments, etc.), suppositories (e.g., rectal suppository, vaginal suppository, etc.), pellets (e.g., pellets for indwelling on retina, etc.), drops, opthalmic topically administered compositions (e.g., eye drops, opthalmic ointment, etc.) and the like.

The pharmaceutical composition can be prepared according to any of the conventional methods in the field of pharmaceutical compositions, for example, according to the procedure described in the Japanese Pharmacopoeia. Hereinafter, a specific method of preparing the pharmaceutical composition will be described in detail.

For example, a pharmaceutical composition to be orally administered is prepared by adding to the active ingredient an excipient (e.g., lactose, sucrose, starch, D-mannitol, etc.), disintegrating agent (e.g., carboxymethyl cellulose calcium, etc.), binder (e.g., α-starch, gum arabic, carboxymethyl cellulose, hydroxypropyl cellulose, polyvinyl-pyrrolidone, etc.), lubricant (e.g., talc, magnesium stearate, polyethyleneglycol 6000, etc.), etc., and compression-molding the mixture composition, and if necessary, coating the composition with a coating base material by a known method so as to mask the taste or allow the composition to dissolve in the intestine or to have persistence.

Examples of the coating base material include sugar coating material, water-soluble film coating material, enteric film coating material, sustained release film coating material, etc.

As the sugar coating material, saccharose is used, which may be used in combination with at least one selected from talc, precipitated calcium carbonate, gelatin, gum arabic, pullulan, carnauba wax. etc.

Examples of the water-soluble film coating material include cellulose polymers such as hydroxypropyl cellulose, hydroxypropylmethyl cellulose, hydroxyethyl cellulose, and methyl hydroxyethyl cellulose; synthesized polymers such as polyvinyl acetal diethylaminoacetate, aminoalkylmethacrylate copolymer E [Eudragit E (trade name), Rhom Pharma], polyvinyl-pyrrolidone, etc.; polysaccharides such as pullulan, etc.

Examples of the enteric film coating material include cellulose polymers such as hydroxypropylmethyl cellulose phthalate, hydroxypropylmethyl cellulose acetate succinate, carboxymethylethyl cellulose, cellulose acetate phthalate, etc.; acrylic polymers such as methacrylate copolymer LD [Eudragit L-30D55 (trade name), Rhom Pharma], methacrylic copolymer S [Eudragit S (trade name), Rhom Pharma]; and natural substances such as shellac, etc.

Examples of the sustained release film coating materials include cellulose polymers such as ethyl cellulose; and acrylate polymers such as aminoalkyl methacrylate copolymer RS[Eudragit RS (trade name), Rhom Pharma], ethyl acrylate.methyl methacrylate copolymer suspension [Eudragit NE (trade name), Rhom Pharma], etc.

Each of the above coating materials may be used as a mixture with at least two thereof in a proper ratio. In addition, a light-shielding material such as titanium oxide, iron sesquioxide or the like may be used in the course of coating.

The injection is prepared by dissolving, suspending or emulsifying the active ingredient in an aqueous solvent (e.g., distilled water, physiological salt solution, Ringer solution, etc.), an oil solvent (e.g., vegetable oils such as olive oil, sesame oil, cotton seed oil, corn oil, and propyleneglycol, etc.) or the like in the presence of a dispersant (e.g., polysorbate 80, polyoxyethylene hardened caster oil 60, etc.), polyethyleneglycol, carboxymethyl cellulose, sodium alginate, etc.), preservative (e.g., methyl paraben, propyl paraben, benzylalcohol, chlorobutanol, phenol, etc.), isotonizing agent (e.g., sodium chloride, glycerin, D-mannitol, D-sorbitol, glucose, etc.) or the like. In this preparation, if necessary, additives such as a solubilizer (e.g., sodium salycylate, sodium acetate, etc.), stabilizer (e.g., human serum albumin, etc.), soothing agent (e.g., benzylalcohol, etc.) and the like may be used.

Preferable examples of the ophthalmic topical agent include eye drops, ophthalmic ointment, etc., and the eye drops may be of aqueous or non-aqueous and in the form of a solution or a suspension. Further, the compound may be dispersed in or adsorbed onto an ophthalmic ointment, gel or a sustained release polymer for use in the composition.

The aqueous eye drops may contain conventional additives such as an isotonizing agent, buffer, pH-adjusting agent, preservative, chelating agent and the like.

Examples of the isotonizing agent include sodium chloride, mannitol, sorbitol, glycerin, etc.; examples of the buffer include phosphate, borate, acetate, citrate, etc.; examples of the pH-adjusting agent include hydrochloric acid, acetic acid, sodium hydroxide, etc.; examples of the preservative include paraoxybenzoic acid esters, benzalkonium chloride, chlorohexydine, benzylalcohol, sorbic acid, or a salt thereof, thiomerosal, chlorobutanol, etc.; and examples of the chelating agent include sodium edetate, sodium citrate, condensed sodium phosphate, etc.

The aqueous eye drops may further contain a thickener or/and a suspending agent, examples of which include methyl cellulose, carmellose or a salt thereof, hydroxyethyl cellulose, sodium alginate, carboxyl vinyl polymer, polyvinylalcohol, polyvinylpyrrolidone, etc.

Further, the aqueous eye drops may contain a surfactant (e.g., polyethyleneglycol, propyleneglycol, polyoxyethylene hardened caster oil, polysorbate 80, etc.), etc.

When the compound is administered in the form of an aqueous suspending eye drops, the above polymer thickener, surfactant and the like may be suitably selected for use in the composition.

When the compound is administered in the form of a non-aqueous eye drops, the solvent therefor is suitably selected from vegetable oils such as caster oil, sesame oil, soybean oil and olive oil, and liquid paraffin, propyleneglycol, β-octyldodecanol and the like for use in the composition.

When the compound is administered in the form of non-aqueous suspending eye drops, the solvent therefor is suitably selected from thixotropic colloids such as aluminum monostearate and the like for use in the composition.

The pH of the above eye drops is adjusted within a range for conventional eye drops, generally 4.0 to 9.0, preferable 5.0 to 8.0.

When the compound is administered in the form of an ophthalmic ointment, the base material therefor is suitably selected from vaseline, plastibase, liquid paraffin and the like for use in the composition.

The base material as the gelling agent of the eye drops is suitably selected from, for example, a carboxyl vinyl polymer, methyl cellulose, sodium alginate, hydroxypropyl cellulose, ethylene maleic anhydride polymer and the like for use in the composition.

The compound having angiotensin II antagonistic activity or prodrug thereof, or a salt thereof [preferably, compounds of the formula and their pharmaceutically acceptable salt] can be used as an agent for preventing, treating or development-inhibiting simple retinopathy or preproliferative retinopathy of mammals (e.g., men, mice, rats, rabbits, dogs, cats, bovines, pigs, monkeys, etc.).

The compound having angiotensin II antagonistic activity or prodrug thereof, or a salt thereof [preferably, compounds of the formula and their pharmaceutically acceptable salt] is useful for preventing, treating or development-inhibiting retinopathies such as angiopathic retinopathy, arteriosclerotic retinopathy, hypertensive retinopathy, diabetic retinopathy, retinopathy of prematurity, renal retinopathy, retinal venous occlusion, and aging macular degeneration, and also useful for preventing, treating or development-inhibiting simple retinopathy or preproliferative retinopathy, in the early stage where no neovascular is observed, because of the excellent retinal potential (visual function)-improving effect and the retinal edema (disorder in tissue)-improving effect.

The dosage of the compound having angiotensin II antagonistic activity or prodrug thereof, or a salt thereof [preferably, compounds of the formula and their pharmaceutically acceptable salt] varies depending on a subject, administration route, disease to be treated, or conditions of the disease. For example, in case of oral administration to a mammal, particularly an adult man (50 kg in weight), generally about 0.001 to about 500 mg, preferably 1 to 50 mg of the above compound or a salt thereof as the active ingredient is administered per one dosage, and it is preferable to administer this dosage of the compound or the salt 1 to 3 times per day.

In case where the compound or a salt thereof is administered in the form of eye drops, the concentration thereof is generally 0.001 to 10 w/v %, preferably 0.01 to 5 w/v %, more preferably 0.1 to 2 w/v %, and it is desirable that 1 to several drops, preferably 1 to 2 drops of such eye drops (the amount of 1 drop is about 50 µl) are administered to an adult man per one time, and that this dosage of the eye drops is administered 3 to 6 times, preferably 4 to 5 times per day. On the other hand, in case where the compound or a salt thereof is administered in the form of an ophthalmic ointment, the concentration of the compound is generally 0.001 to 10 w/v %, preferably 0.01 to 5 w/v %, more preferably 0.1 to 2 w/v %, and it is preferable that such ointment is administered to the conjunctival sac in a dosage of about 0.1 to about 0.2 g per time, and that this dosage of the ointment is administered 1 to 4 times per day.

BEST MODE FOR CARRYING OUT THE INVENTION

The present invention is hereinafter described in more detail by means of the following Examples and Test Examples, which are not to be construed as limitative.

EXAMPLES

Test Example 1

Inhibition of Retinal VEGF Production and Improvement of Retinal Potential on Diabetic Rats
Compound 1: (±)-1-(cyclohexyloxycarbonyloxy) ethyl-2-ethoxy-1-[[2'-(1H-tetrazol-5-yl)biphenyl-4-yl]methyl]-1H-benzimidazole-7-carboxylate (Compound 1)

Method: Streptozotocin (STZ) was intravenously injected at a dose of 30 mg/kg to 10-week old male rats (Stroke-Prone Spontaneously Hypertensive Rat:SHRSP). When 9 weeks had passed since the injection of STZ, the blood sugar values of the rats were measured. The rats were divided into 3 groups, that is, a group before the administration, a solvent-administered control group and an administered group with the compound 1 (3 mg/kg/day, p.o.). Four weeks after, the blood sugar values and the retinal potentials were measured, and then, the rats were killed by bleeding by discission of the aorta abdominalis under deep ether anesthetization so as to remove the eyeball. A suspension of the compound 1 in a 0.5% methylcellulose-containing physiological saline was orally administered to the rats once a day for 4 weeks. On the other hand, 23-week old SHRSP rats were used as an untreated group.

The blood sugar value was measured by the following method. The blood was collected from the veins of the tails using heparin and subjected to centrifugation to collect the blood plasma. The amount of glucose in the plasma was measured using an autoanalyzer (Model 7070, manufactured by Hitachi Seisakusho).

The retinal potential was measured by the following method. The subject animal was subjected to dark adaptation in a dark room for 90 to 120 minutes, and then, anesthetized with ketamine hydrochloride (50 mg/kg, i.m.) and immobilized with xylazine (2 mg/kg, i.m.). The limb and the head of the subject animal were fixed with a string. Mydriatic was dropped on the left eyeball to widen the pupil, and a contact lens type electrode was placed on the cornea using a contact lens-wearing auxiliary. A xenon lamp (1.2 joules) was set at a position 10 cm distant in the forward direction from the eye to be tested (the left eye), and light stimuli were controlled by a light stimulator (SLS-3100 manufactured by Nippon Koden K.K.). The retinal potential generated by light stimuli (0.5 Hz, 16 times) was amplified by a Neuropack (MEB-5100 manufactured by Nippon Koden K.K., Low cut 0.5 Hz, and sweeping time: 200 msec). The results were added and averaged. The latency of oscillatory potential peaks (O1, O2 and O3) was counted from the resultant waveforms.

VEGF mRNA in the retina was quantitatively determined as follows. RNA was extracted from the removed eyeball using ISOGEN (Nippon Gene). The quantity of VEGF mRNA was measured from the extracted RNA by the semi-quantitative RT-PCR process (ABI PRISM 7700: Perkin Elmer) using two kinds of fluorescent probes (FAM: VEGF, and VIC: β-action). The quantity of VEGF mRNA was corrected by the quantity of β-action mRNA and calculated provided that the quantity of VEGF mRNA of SD rat retina was defined as 1.

The Dunnett's t Test was employed for statistical significant difference test.

Evaluation: Shown in Table 1.

The concentrations of glucose in the plasma show marked hyperglycemia in the group before the administration, the control group and the administered group with the compound 1, and thus, there was no difference in concentration between each of the 3 groups. The latencies of the oscillatory potential peaks were prolonged in any of O1, O2 and O3 in the group before the administration and the control group, as compared with the untreated group. The latency was reduced in any of the O1, O2 and O3 in the administered group with the compound 1, and a significant improvement was observed particularly in O1 as compared with that of the control group. The quantities of VEGF mRNA in the retinal tissues of the group before the administration and the control group were markedly increased as compared with the normal value (the quantity of VEGF mRNA in the retinal tissue of the SD rat was determined as 1). The quantity of VEGF mRNA in the retinal tissue of the administered group with the compound 1 was significantly decreased, and it was recovered to the normal level.

TABLE 1

Action of Compound 1 on Plasma Glucose, Retinal VEGF mRNA and Latency of Oscillatory Potential Peak of Diabetic Rats

|  | Group before the administration (n = 5) | Control group (n = 5) | Administered group with compound 1 (n = 4) | Untreated group (n = 5) |
|---|---|---|---|---|
| Plasma glucose (mg/dl) | 526.1 ± 36.9 | 571 ± 66 | 525 ± 35 | 142 ± 10 |
| Retinal VEGF mRNA (VEGF mRNA of SD rat determined as 1) | 1.50 ± 0.39 | 1.46 ± 0.14 | 0.99 ± 0.14** | 1.08 ± 0.05 |

TABLE 1-continued

Action of Compound 1 on Plasma Glucose, Retinal VEGF mRNA
and Latency of Oscillatory Potential Peak of Diabetic Rats

| | Group before the administration (n = 5) | Control group (n = 5) | Administered group with compound 1 (n = 4) | Untreated group (n = 5) |
|---|---|---|---|---|
| Latency of oscillatory potential peak | | | | |
| O1 (ms) | 27.06 ± 2.49 | 25.66 ± 0.87 | 23.81 ± 0.42* | 23.76 ± 0.80 |
| O2 (ms) | 35.32 ± 2.91 | 34.88 ± 1.64 | 32.88 ± 1.17 | 32.13 ± 0.65 |
| O3 (ms) | 45.25 ± 3.43 | 46.04 ± 1.35 | 43.39 ± 1.86 | 43.83 ± 1.61 |

The values were calculated by the equation of an average ± standard deviation.
Test of significant difference from a value equivalent to each of the values of the control group:
*$P < 0.05$
**$P < 0.01$ The pharmaceutical composition for preventing, treating or development-inhibiting simple retinopathy or preproliferative retinopathy, comprising the compound having angiotensin II antagonistic activity or prodrug thereof, or a salt thereof, [preferably the compound of the formula (1) or a pharmaceutical acceptable salt thereof] as an active ingredient was prepared, for example, by the following formulation.

Example 1

| Capsule: | |
|---|---|
| (1) Compound 1 | 30 mg |
| (2) Lactose | 90 mg |
| (3) Fine crystal cellulose | 70 mg |
| (4) Magnesium stearate | 10 mg |
| 1 capsule | 200 mg |

The ingredients (1), (2) and (3) and a half of the ingredient (4) were admixed and the admixture was granulated. The remaining ingredient (4) was added to the granules, and a whole of the granular mixture was encapsulated in gelatin capsules.

Example 2

| Tablet: | |
|---|---|
| (1) Compound 1 | 30 mg |
| (2) Lactose | 35 mg |
| (3) Corn starch | 150 mg |
| (4) Fine crystal cellulose | 30 mg |
| (5) Magnesium stearate | 5 mg |
| 1 tablet | 250 mg |

The ingredients (1), (2) and (3) and two thirds of the ingredient (4) and a half of the ingredient (5) were admixed, and the admixture was granulated. The remaining ingredients (4) and (5) were added to the granules, and the granular mixture was molded under pressure to form tablets.

Example 3

| Suspended eye drops | |
|---|---|
| (1) Compound 1 | 1.0 g |
| (2) Sodium dihydrogenphosphate | 0.2 g |
| (3) Sodium chloride | 0.9 g |
| (4) Polysorbate 80 | 0.1 g |
| (5) Benzalkonium chloride | 0.005 g |
| (6) Sodium edetate | 0.01 g |
| (7) 1N sodium hydroxide | proper |
| (8) Sterilized purified water | 100 ml as a whole |

The ingredients (2), (3), (4), (5) and (6) were dissolved in about 80 ml of sterilized purified water (8), and the solution was adjusted to pH 7 with 1N sodium hydroixde (7). The remaining sterilized purified water (8) was added to the solution. The solution was filtered with a membrane filter of 0.2 μm. The compound (1) previously sterilized was suspended in this solution to prepare the suspended eye drops.

INDUSTRIAL APPLICABILITY

The pharmaceutical composition of the present invention exhibits excellent improving actions on retinal potential (visual function) and retinal edema (disorder in tissue), and can be advantageously used for preventing, treating or development-inhibiting simple retinopathy or preproliferative retinopathy.

The invention claimed is:

1. A method for improving retinal potential or retinal edema in a mammal in need thereof, which comprises administering to the mammal an effective amount of a compound having angiotensin II antagonistic activity, wherein the compound having angiotensin II antagonistic activity is

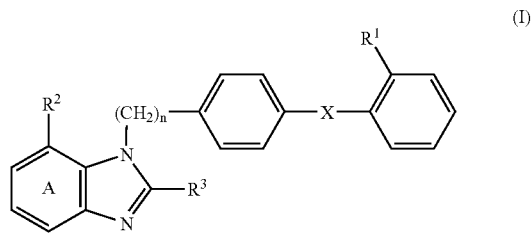

(I)

2-ethoxy-1-[[2'-(1H-tetrazol-5-yl)biphenyl-4-yl]methyl]benzimidazole-7-carboxylic acid, a prodrug thereof or a pharmaceutically acceptable salt thereof.

2. The method according to claim 1, wherein the compound having angiotensin II antagonistic activity is 1-(cyclohexyloxycarbonyloxy)ethyl 2-ethoxy-1-[[2'-(1H-tetrazol-5-yl)biphenyl-4-yl]methyl]benzimidazole-7-carboxylate.

* * * * *